(12) United States Patent
Rotem et al.

(10) Patent No.: US 8,012,500 B2
(45) Date of Patent: Sep. 6, 2011

(54) IMPLANTABLE DEVICE

(75) Inventors: Avi Rotem, Petach-Tikva (IL); Yoav Evron, Hod-Hasharon (IL); Pnina Vardi, Haifa (IL); Konstantin Bloch, Petach-Tikva (IL)

(73) Assignee: Beta-O2 Technologies Ltd., Kiryat Arye, Petach-Tikva (IL)

( * ) Notice: Subject to any disclaimer, the term of this patent is extended or adjusted under 35 U.S.C. 154(b) by 2045 days.

(21) Appl. No.: 11/001,556

(22) Filed: Nov. 30, 2004

(65) Prior Publication Data

US 2005/0136092 A1 Jun. 23, 2005

Related U.S. Application Data

(63) Continuation-in-part of application No. 10/466,069, filed as application No. PCT/IL01/00031 on Jan. 12, 2001, now Pat. No. 7,892,222.

(30) Foreign Application Priority Data

Jan. 1, 2000 (IL) .......................................... 134009

(51) Int. Cl.
*A61F 2/00* (2006.01)
(52) U.S. Cl. ............................. 424/423; 604/22; 604/23
(58) Field of Classification Search ........... 604/288.01–288.04, 22–24, 26, 604/890.1–891.1; 424/422–425, 195.17
See application file for complete search history.

(56) References Cited

U.S. PATENT DOCUMENTS

| 4,352,883 A | 10/1982 | Lim |
| 4,402,694 A | 9/1983 | Ash et al. |
| 4,631,053 A | 12/1986 | Taheri |
| 5,011,472 A | 4/1991 | Aebischer et al. |
| 5,101,814 A | 4/1992 | Palti |
| 5,116,494 A | 5/1992 | Chick et al. |
| 5,262,055 A | 11/1993 | Bae et al. |
| 5,336,209 A | 8/1994 | Porzilli |
| 5,427,935 A | 6/1995 | Wang et al. |
| 5,443,508 A | 8/1995 | Giampapa |
| 5,713,888 A | 2/1998 | Neuenfeldt et al. |
| 5,741,334 A | 4/1998 | Mullon et al. |
| 5,792,090 A | 8/1998 | Ladin |
| 5,834,005 A | 11/1998 | Usala |
| 5,855,070 A | 1/1999 | Grabowski |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 6,000,403 A | 12/1999 | Cantwell |
| 6,091,974 A | 7/2000 | Palti |

(Continued)

FOREIGN PATENT DOCUMENTS

GB          2 024 012 A          1/1980

(Continued)

OTHER PUBLICATIONS

Klueh, et al., "Enhancement of implantable glucose sensor function in vivo using gene transfer-included neovascularization", Biomaterials, vol. 26, No. 10, Apr. 2005. (an abstract).

(Continued)

*Primary Examiner* — Theodore Stigell (74) *Attorney, Agent, or Firm* — Fish & Richardson P.C.

(57) ABSTRACT

Apparatus is provided including a chamber, which is adapted to be implanted in a body of an individual, the chamber including functional cells and chlorophyll-containing elements comprising chlorophyll of an obligate photoautotroph.

30 Claims, 2 Drawing Sheets

U.S. PATENT DOCUMENTS

| | | | |
|---|---|---|---|
| 6,148,232 | A | 11/2000 | Avrahami |
| 6,368,592 | B1 | 4/2002 | Colton et al. |
| 6,372,244 | B1 | 4/2002 | Antanavich et al. |
| 6,767,342 | B1 | 7/2004 | Cantwell |
| 2003/0050622 | A1 | 3/2003 | Humes et al. |
| 2004/0109302 | A1 | 6/2004 | Yoneda et al. |
| 2004/0133188 | A1 | 7/2004 | Vardi et al. |
| 2005/0136092 | A1 | 6/2005 | Rotem et al. |
| 2007/0190038 | A1 | 8/2007 | Suzuki |
| 2008/0086042 | A1 | 4/2008 | Brister et al. |
| 2009/0012502 | A1 | 1/2009 | Rotem et al. |

FOREIGN PATENT DOCUMENTS

| | | |
|---|---|---|
| WO | WO-90/15526 A1 | 12/1990 |
| WO | WO9219195 A1 | 11/1992 |
| WO | WO9420076 A1 | 9/1994 |
| WO | WO-00/78920 | 12/2000 |
| WO | WO-01/50983 A1 | 7/2001 |
| WO | WO-03/011445 A2 | 2/2003 |
| WO | 2009031154 | 3/2009 |

OTHER PUBLICATIONS

Stagner, et al., "The pancreas as an islet transplantation site", Sep. 1, 2007, Journal of the Pancreas, vol. 8, No. 5, pp. 628-636.

European Search Report dated Mar. 27, 2006 (3 pages).

International Search Report (PCT/IL05/01262) dated Apr. 17, 2006.

Wu, Haiyan, et al., "In Situ Electrochemical Oxygen Generation with an Immunoisolation Device", Ann. NY Acad. Sci., 1999, vol. 875, pp. 105-125.

Leheninger, L., Biochemistry, 2nd edition, Worth Publishers, Inc., 1978, Chapter 14, pp. 363-364.

Smith, Arnold J., et al., "Acetate Assimilation by *Nitrobacter agilis* in Relation to Its "Obligate Autotrophy"", Journal of Bacteriology, Mar. 1968, vol. 95, No. 3, p. 844.

IMPLANTABLE DEVICE

CROSS-REFERENCES TO RELATED APPLICATIONS

The present patent application is a continuation-in-part of U.S. patent application Ser. No. 10/466,069, filed Mar. 12, 2004 now U.S. Pat. No. 7,892,222 entitled, "Implantable device," which is a US national phase application of PCT Patent Application PCT/IL 2001/00031 filed Jan. 12, 2001, and is incorporated herein by reference.

FIELD OF THE INVENTION

The present invention relates generally to implantable medical devices, and specifically to implantable medical devices containing living cells.

BACKGROUND OF THE INVENTION

Oxygen is essential to many physiological and metabolic processes, including aerobic metabolism. A lack of oxygen often leads to cell injury or death. Oxygen serves an important role in wound healing, including collagen production by fibroblasts, neovascularization, and polymorphonuclear cell function. Hyperbaric oxygen therapy is sometimes used for wound healing in cases that have failed to respond to conventional treatment techniques.

Several disorders are caused by hyposecretion of one or more substances such as hormones. For example, hyposecretion of a hormone by the following cells may cause a disorder: pancreatic islet cells, hepatocytes, thyroid cells, parathyroid cells, neural cells, ovarian cells, adrenal cells, renal cortex cells, vascular endothelial cells, thymic cells, ovarian cells, and testicular cells. These disorders include diabetes, Parkinson's disease, Alzheimer's disease, hypo- and hypertension, hypothyroidism, and various liver disorders. The hormone insulin, for example, is produced by beta cells in the islets of Langerhans of the pancreas. In normal individuals, insulin release is regulated so as to maintain blood glucose levels in the range of about 70 to 110 milligrams per deciliter. In diabetics, insulin is either not produced at all (Type I diabetes), or the body cells do not properly respond to the insulin that is produced (Type II diabetes). The result is elevated blood glucose levels.

Disorders arising from hyposecretion of a hormone are usually treated by administration of the hormone. However, despite advances in understanding and treating many of these disorders, it is often not possible to precisely regulate metabolism with exogenous hormones. A diabetic, for example, is required to make several daily measurements of blood glucose levels and then inject an appropriate amount of insulin to bring the insulin and glucose levels to within the acceptable range.

Organ transplantation is not a viable treatment today for most of these disorders for several reasons, including the rejection of a transplanted organ by the immune system. Isolated cells may be implanted in the body, in combination with treating the patient or the cells to prevent rejection, e.g., by encapsulating the cells, or by applying immunosuppressants or radiation to the patient.

PCT Publication WO 01/50983 to Vardi et al., and U.S. patent application Ser. No. 10/466,069 in the national phase thereof, which are assigned to the assignee of the present application and are incorporated herein by reference, describe an implantable device comprising a chamber for holding functional cells and an oxygen generator for providing oxygen to the functional cells. In one embodiment, the oxygen generator comprises photosynthetic cells that convert carbon dioxide to oxygen when illuminated. In another embodiment, the oxygen generator comprises electrodes that produce oxygen by electrolysis.

U.S. Pat. No. 6,368,592 to Colton et al., which is incorporated herein by reference, describes techniques for supplying oxygen to cells in vitro or in vivo by generating oxygen with an oxygen generator that electrolyzes water to oxygen and hydrogen. The oxygen generator may be used to supply oxygen to cells contained in an encapsulating chamber for implanting in the body such as an immunoisolation chamber bounded by a semipermeable barrier layer that allows selected components to enter and leave the chamber. A bioactive molecule may be present with the cells.

U.S. Pat. No. 5,443,508 to Giampapa, which is incorporated herein by reference, describes an implantable biological agent delivery system. The system includes a pod adapted for subcutaneous implantation beneath the dermis of the skin. The pod includes a porous surface and has at least one internal chamber which is in fluid communication with the porous surface. The system includes a dome adapted to be detachably secured to the chamber. The dome includes interior chambers, each in fluid communication with the interior of the pod. Prior to implantation, the chambers are loaded with bioactive agents, such as hormones, enzymes, biologic response modifiers, free radical scavengers, or genetically altered cell cultures. Time-release micropumps pump the agents into the interior chambers of the pod for transmission through the porous surfaces into a growth factor-stimulated capillary matrix and then to the bloodstream of the subject. The pod may be removed, refilled, and resecured to the dome upon exhaustion of its contents or upon medical requirement for changes in medication, or may be percutaneously refilled in situ through injection into the dome. The surface of the pod may be treated with one or more vascular growth factors or related biologic molecules.

U.S. Pat. No. 5,614,378 to Yang et al., which is incorporated herein by reference, describes a photobioreactor system for oxygen production for a closed ecological life support system. The photobioreactor is described, among other things, as being useful for converting carbon dioxide to oxygen in an artificial lung.

U.S. Pat. No. 4,721,677 to Clark, Jr., which is incorporated herein by reference, describes an implantable biosensor and method for sensing products, such as hydrogen peroxide, generated from an enzymatic reaction between an analyte, like glucose, and an enzyme in the presence of oxygen. The biosensor is equipped with an enclosed chamber for containing oxygen and can be adapted for extracting oxygen from animal tissue adjacent the container. The biosensor is designed to optically or electrically sense products generated from the enzymatic reaction which serve as a function of the analyte.

PCT Publication WO 03/011445 to Monzyk et al., which is incorporated herein by reference, describes a photolytic cell and a photolytic artificial lung incorporated the photolytic cell.

PCT Publication WO 90/15526 to Kertz, which is incorporated herein by reference, describes an integument and related process for the culturing and growing of living organic material. The integument includes a cellule made of a gas-permeable, liquid- and contaminant-impermeable membrane for completely enclosing and sealing the culture from biological contaminants in the ambient environment. The membrane allows gas exchange between the living organic material and the ambient environment to provide enhanced growth and the prevention of contamination.

Wu H et al., in "In situ electrochemical oxygen generation with an immunoisolation device," Ann N Y Acad Sci 875: 105-25 (1999), which is incorporated herein by reference, describe an in situ electrochemical oxygen generator which decomposes water electrolytically to provide oxygen to the adjacent planar immunobarrier diffusion chamber. In vitro culture experiments were carried out with beta TC3 cells encapsulated in titanium ring devices. The growth and viability of cells with or without in situ oxygen generation was studied.

Methods for immunoprotection of biological materials by encapsulation are described, for example, in U.S. Pat. Nos. 4,352,883, 5,427,935, 5,879,709, 5,902,745, and 5,912,005, all of which are incorporated herein by reference. The encapsulating material is typically selected so as to be biocompatible and to allow diffusion of small molecules between the cells of the environment while shielding the cells from immunoglobulins and cells of the immune system. Encapsulated beta cells, for example, can be injected into a vein (in which case they will eventually become lodged in the liver) or embedded under the skin, in the abdominal cavity, or in other locations. Fibrotic overgrowth around the implanted cells, however, gradually impairs substance exchange between the cells and their environment. Hypoxia of the cells typically leads to cell death.

U.S. Pat. No. 5,855,613 to Antanavich et al., which is incorporated herein by reference, describes embedding cells in a thin sheet of alginate gel that is then implanted in a body.

U.S. Pat. No. 5,834,005 to Usala, which is incorporated herein by reference, describes immunoisolating cells by placing them in a chamber that is implanted inside the body. In the chamber, the cells are shielded from the immune system by means of a membrane permeable to small molecules such as glucose, oxygen, and the hormone secreted by the cells, but impermeable to cells and antibodies.

U.S. Pat. No. 5,101,814 to Palti, which is incorporated herein by reference, describes the use of a chamber for implanting glucose-sensitive cells into the body, and monitoring an optical or electrical property of the cells that is correlated with glucose levels.

U.S. Pat. Nos. 6,091,974 and 5,529,066 to Palti, which are incorporated herein by reference, describe a capsule for encapsulating implantable cells for improving the detectability of electrical signals generated by the cells. The capsule includes a low-conductivity (high electrical resistance) membrane and a semi-permeable (low electrical resistance) membrane. The low-conductivity membrane seals around the circumference of the cell mass between the electrical poles of the capsule, and further extends for increasing the electrical resistance between the poles. The semi-permeable membrane enables nutrients and waste materials to flow to and from the cell mass. The semi-permeable membrane encloses at least one of the poles of the cell mass, and cooperates with the low-conductivity membrane to completely enclose the cell mass. The low-conductivity membrane may enclose one of the poles, if desired. Electrodes are used to detect the electrical signals from the cell mass.

U.S. Pat. No. 4,402,694 to Ash et al., which is incorporated herein by reference, describes a body cavity access device for supplying a hormone to a patient. The device includes an implantable housing placed in the body and having an impermeable extracorporeal segment and a semipermeable subcutaneous segment. A hormone source such as live, hormone-producing cells, e.g., pancreatic islet cells, is then removably positioned in the housing to provide a hormone supply to the patient. A sensor can be located within the subcutaneous segment and operably associated with a dispenser to release medication into the housing and to the patient.

U.S. Pat. No. 5,011,472 to Aebischer et al., which is incorporated herein by reference, describes techniques for providing hybrid, modular systems for the constitutive delivery of active factor to a subject and, in some instances, to specific anatomical regions of the subject. The systems include a cell reservoir containing living cells capable of secreting an active agent, which is preferably adapted for implantation within the body of the subject and further includes at least one semipermeable membrane, whereby the transplanted cells can be nourished by nutrients transported across the membrane while at the same time protected from immunological, bacterial, and viral assault. The systems further include a pumping means, which can be implantable or extracorporeal, for drawing a body fluid from the subject into the cell reservoir and for actively transporting the secreted biological factors from the cell reservoir to a selected region of the subject.

U.S. Pat. No. 5,116,494 to Chick et al., which is incorporated herein by reference, describes a device that serves as an artificial pancreas. The device comprises a hollow fiber which is surrounded by islets of Langerhans enclosed in a housing. The islets are suspended in a temperature sensitive matrix which is sufficiently viscous to support islets at a temperature below about 45 degrees C. and sufficiently fluid to enable removal of islet suspension at a temperature above about 45 degrees C. A warm (e.g., 48 degree to 50 degree C. solution) may be flushed through the device to change the physical state of the temperature sensitive matrix from a semi-solid state to a liquefied semi-gel state. The temperature sensitive supporting material is described as enabling long-term maintenance of islet cells in in vitro culture.

U.S. Pat. No. 5,741,334 to Mullon et al., which is incorporated herein by reference, describes an artificial pancreatic perfusion device comprising a hollow fiber having a porosity ranging from about 25 Kd to about 200 Kd. The hollow fiber has one end connected to a blood vessel for receiving blood and a second end connected to a blood vessel for returning the blood. Islets of Langerhans surround the hollow fiber. The hollow fiber and islets are surrounded by a housing comprising a semipermeable membrane having a pore size small enough to offer protection to the islets and host from immune reactive substances.

U.S. Pat. No. 5,702,444 to Struthers et al., which is incorporated herein by reference, describes an implantable artificial endocrine pancreas comprising a reactive body of soft, plastic, biocompatible, porous hydratable material supporting a multiplicity of endocrine pancreatic islets in isolated spaced relationship from each other, and a microporous barrier membrane enveloping and supporting the body, in spaced relationship from the pancreatic islets therein and through which molecules having a molecular weight greater than 60,000 Daltons cannot penetrate.

U.S. Pat. No. 6,630,154 to Fraker et al., which is incorporated herein by reference, describes a composition including at least one glycosaminoglycan, e.g., CIS, at least one perfluorinated substance and at least one alginate, e.g., sodium alginate.

US Patent Application Publication 2004/0109302 to Yoneda et al., which is incorporated herein by reference, describes a plant cultivation method, including cultivating plants with irradiating pulsed light with a period of 2 microseconds to 1 millisecond and a duty ratio of 20% to 70%, using a light emitting diode that emits white light or light of two colors.

U.S. Pat. No. 5,381,075 to Jordan, which is incorporated herein by reference, describes a method for driving an immersed flashing light system to enhance algae growth. The flashing light system includes a plurality of light source elements that are arranged to illuminate the algae. The light source elements are electrically connected to form banks of light source elements. Power is supplied to each bank of light sources in a predetermined sequence at regular intervals to substantially evenly supply each bank of light source elements with a series of power pulses, while maintaining a substantially continuous load on the power supply. The power pulses are substantially half cycles of a square wave.

SUMMARY OF THE INVENTION

In some embodiments of the present invention, apparatus comprises a chamber, which is adapted to be implanted in a body of a subject, the chamber comprising one or more types of functional cells, and chlorophyll-containing elements. Typically, the chlorophyll-containing elements include intact photosynthetic cells (e.g., photosynthetic cells of unicellular or multicellular algae) and/or isolated chloroplasts. The chlorophyll-containing elements provide oxygen to the functional cells and/or consume carbon dioxide produced by the functional cells. The chamber has one or more walls that are adapted to be permeable to nutrients and substances produced or secreted by the cells. The walls also typically immunoisolate the cells from constituents of the body. For some applications, the chamber is adapted to be implanted under skin of the subject, or in the peritoneum. For some applications, the chamber is shaped as a prism, an elongated tubular element, a wafer, a sphere, or another shape appropriate for the particular application.

In some embodiments of the present invention, the apparatus further comprises a light source that is adapted to provide light to the chlorophyll-containing elements. For some applications, the apparatus additionally comprises a control unit, which is adapted to drive the light source to provide the light. In some embodiments, the control unit is configured to drive the light source to provide the light in a series of pulses. For some applications, the control unit adjusts one or more parameters of the pulses responsively to one or more sensed parameters of the functional cells and/or the chlorophyll-containing elements. For example, the chamber may comprise an oxygen sensor that detects an oxygen concentration in a vicinity of the functional cells, and/or in a vicinity of the chlorophyll-containing elements. Providing the light in the series of pulses generally reduces power consumption of the apparatus, and/or provides control of the quantity of oxygen produced by the chlorophyll-containing elements, and/or provides control of the quantity of carbon dioxide consumed by the chlorophyll-containing elements.

In some embodiments of the present invention, the chamber comprises an oxygen reservoir, which typically comprises a material that stores and releases oxygen, such as responsively to an oxygen concentration in a vicinity of the reservoir. The oxygen reservoir typically stores oxygen produced by the chlorophyll-containing elements that is in excess of the current needs of the functional cells, and releases the stored oxygen if insufficient oxygen is later generated by the chlorophyll-containing elements.

For some applications, but not necessarily, the chlorophyll-containing elements include chlorophyll of an obligate photoautotroph. As used in the present application, including the claims, an obligate photoautotroph is an organism that, under conditions of ordinary use of the apparatus described herein, produces energy substantially only by photosynthesis, and substantially cannot use organic materials in the surrounding environment as a source of energy. As a result, such obligate photoautotrophs are substantially unable to grow in organic media in the dark. (See, for example, Smith A J, "Acetate assimilation by *Nitrobacter agilis* in relation to its 'obligate autotrophy,'" Journal of Bacteriology 95:844-855 (1968), which is incorporated herein by reference.) Appropriate obligate photoautotrophs include, but are not limited to, certain of the cyanobacteria (formerly called blue-green algae), e.g., *Synechococcus*, certain of the *Thiobacilli*, and bacteria of the genus *Chlorobium*.

Alternatively or additionally, the chlorophyll-containing elements include chlorophyll of unicellular algae, or chlorophyll of other autotrophic or mixotrophic or facultative photosynthetic cells.

Typically, the chamber is adapted to hold the functional cells mixed with the chlorophyll-containing elements. Alternatively, the chamber comprises two or more compartments, some of which hold functional cells and others of which hold the chlorophyll-containing elements. For some applications, the functional cells and/or the chlorophyll-containing elements are dispersed within a liquid medium or matrix in the chamber. Alternatively or additionally, the functional cells and/or chlorophyll-containing elements are coupled to a substrate, such as one or more walls of the chamber.

In some embodiments of the present invention, the functional cells include beta cells, alpha cells, other pancreatic islet cells, hepatic cells, neural cells, renal cortex cells, vascular endothelial cells, thyroid cells, parathyroid cells, adrenal cells, thymic cells, ovarian cells, and/or testicular cells.

In some embodiments of the present invention, the apparatus is configured to:

treat a condition characterized by an insufficiency or lack of a natural population of the functional cells, or by reduced effectiveness of such cells, which results in an insufficient supply of a beneficial substance secreted by the cells, such as a hormone or a neurotransmitter. The functional cells held in the chamber secrete the beneficial substance. For example, the functional cells may include beta cells, and the apparatus may be configured to treat type I or type II diabetes.

treat a condition characterized by an insufficiency or lack of a natural population of the functional cells, or by reduced effectiveness of such cells, which results in insufficient uptake, absorption, and/or degradation of a substance (e.g., a toxic substance) by the cells. For example, the functional cells may include hepatic cells, and the apparatus may be configured to uptake various toxic substances.

sense a level of a bodily constituent to which the functional cells are sensitive. The apparatus is configured to sense the constituent by monitoring a property of the functional cells and/or of the chlorophyll-containing elements that generally correlates with a level of the constituent. For example, the apparatus may monitor a level of oxygen produced by the chlorophyll-containing elements. Alternatively or additionally, the apparatus is adapted to use techniques for monitoring an electrical or optical property of the functional cells to detect a constituent such as glucose, as described in the above-mentioned U.S. Pat. No. 5,101,814. For some applications, the functional cells include beta cells, and the apparatus is configured to sense a glucose level by directly or indirectly monitoring activity of the beta cells.

In some embodiments of the present invention, apparatus comprises a chamber, which is adapted to hold functional cells, and to be implanted under skin in a body of a subject, and an oxygen generator, adapted to be placed outside the body in a vicinity of the skin.

There is therefore provided, in accordance with an embodiment of the present invention, apparatus including a chamber, which is adapted to be implanted in a body of an individual, the chamber including:

functional cells; and chlorophyll-containing elements including chlorophyll of an obligate photoautotroph.

For some applications, the functional cells include a single cell type. Alternatively, the functional cells include a plurality of cell types.

For some applications, the chlorophyll-containing elements include chlorophyll of a unicellular obligate photoautotroph. Alternatively or additionally, the chlorophyll-containing elements include chlorophyll of a multicellular obligate photoautotroph.

For some applications, the chlorophyll-containing elements are positioned in a vicinity of the functional cells in a manner that facilitates providing of oxygen by the chlorophyll-containing elements to the functional cells. Alternatively or additionally, the chlorophyll-containing elements are positioned in a vicinity of the functional cells in a manner that facilitates consumption by the chlorophyll-containing elements of carbon dioxide produced by the functional cells.

For some applications, the functional cells are mixed with the chlorophyll-containing elements. For some applications, the functional cells are not immunoisolated from the chlorophyll-containing elements.

For some applications, the chamber includes a liquid medium, in which the functional cells are dispersed. For some applications, the chamber includes a matrix, in which the functional cells are dispersed. For some applications, the chamber includes a substrate, to which the functional cells are attached.

For some applications, the chamber includes one or more walls, adapted to immunoisolate the functional cells from constituents of the body.

For some applications, the chamber is adapted to be implanted subcutaneously in the body. Alternatively, the chamber is adapted to be implanted in peritoneum of the body.

For some applications, the chamber includes a gel matrix, in which the functional cells and the chlorophyll-containing elements are embedded.

For some applications, the chlorophyll-containing elements include chlorophyll of a genetically-engineered obligate photoautotroph.

For some applications, the chamber is prism-shaped. For some applications, the chamber includes an oxygen reservoir. For some applications, the apparatus includes a rechargeable battery. For some applications, the chamber is coated with a vascular growth factor.

For some applications, the obligate photoautotroph includes bacteria of the genus *Thiobacilli*. Alternatively or additionally, the obligate photoautotroph includes bacteria of the genus *Chlorobium*. Further alternatively or additionally, the obligate photoautotroph includes cyanobacteria. For some applications, the cyanobacteria include cyanobacteria of the genus *Synechococcus*.

For some applications, at least a portion of the chlorophyll-containing elements include intact cells of the obligate photoautotroph. For some applications, the chamber includes between 10,000 and 600,000 pancreatic islets. Alternatively, the chamber includes fewer than 10,000 pancreatic islets.

For some applications, the chamber includes a membrane, configured to separate the functional cells from the chlorophyll-containing elements. For some applications, the membrane is configured to permit passage of a gas therethrough.

In an embodiment, the apparatus includes a light source, configured to provide light to the chlorophyll-containing elements. For some applications, the apparatus includes a control unit, adapted to drive the light source to provide the light in a series of pulses. Alternatively or additionally, the apparatus includes a control unit, adapted to drive the light source to provide the light intermittently during alternating "on" and "off" periods.

For some applications, the apparatus includes a control unit, adapted to control a level of oxygen provided by the chlorophyll-containing elements, by controlling a level of the light provided by the light source. For some applications, the light source is physically coupled to the chamber. Alternatively, the light source is configured to be implanted in the body in a vicinity of the chamber. Further alternatively, the light source is configured to be placed external to the body in a vicinity of the chamber.

In an embodiment, the functional cells are capable of releasing a substance, and the chamber includes one or more walls that are permeable to the substance and are substantially not permeable to the functional cells, such that the substance is released to the body. For some applications, the functional cells are selected from the list consisting of: pancreatic islet cells, hepatocytes, thyroid cells, parathyroid cells, neural cells, ovarian cells, adrenal cells, renal cortex cells, vascular endothelial cells, thymic cells, ovarian cells, testicular cells, genetically engineered cells, cloned cells, and stem cells. Alternatively, the functional cells include pancreatic beta cells. For some applications, the chamber includes between 10 million and 600 million of the beta cells. Alternatively, the chamber includes fewer than 10 million of the beta cells.

For some applications, the chamber includes pancreatic islets containing the beta cells. For some applications, the chamber includes between 10,000 and 600,000 of the islets. Alternatively, the chamber includes fewer than 10,000 of the islets.

In an embodiment, the functional cells are capable of performing at least one of the actions selected from the list consisting of: absorbing a substance from the body, and degrading a substance from the body. For some applications, the functional cells include hepatic cells.

In an embodiment, the apparatus includes an oxygen sensor for determining an oxygen concentration in a vicinity of the functional cells. For some applications, the apparatus includes a control unit configured to activate the chlorophyll-containing elements when the oxygen concentration in the vicinity of the functional cells is below a first threshold, and to inactivate the chlorophyll-containing elements when the oxygen concentration in the vicinity of the functional cells is above a second threshold. For some applications, the apparatus includes a light source, and the control unit is adapted to control a level of oxygen provided by the chlorophyll-containing elements by controlling a level of light generated by the light source. For some applications, the first threshold is between 30 and 50 mmHg, and the second threshold is between 80 and 100 mmHg.

For some applications, the apparatus includes a control unit adapted to determine an indication of a level in the body of a substance to which the functional cells are sensitive. For some applications, the control unit is adapted to determine the indication by monitoring a property selected from the list consisting of: a property of the functional cells, and a property of the chlorophyll-containing elements. For some applications, the property of the functional cells includes an electrical property of the functional cells, and the control unit is adapted to monitor the electrical property of the functional cells. Alternatively, the property of the functional cells includes an optical property of the functional cells, and the control unit is adapted to monitor the optical property of the functional cells. For some applications, the substance includes glucose, and the control unit is adapted to determine the indication of the level of the glucose. For some applications, the functional cells include pancreatic beta cells.

There is also provided, in accordance with an embodiment of the present invention, apparatus for use with functional cells, the apparatus including a chamber, which is adapted to be implanted in a body of an individual, and to hold the functional cells, the chamber including chlorophyll-containing elements containing chlorophyll of an obligate photoautotroph.

For some applications, the functional cells include autologous functional cells of the individual, and the chamber is adapted to hold the autologous functional cells.

There is further provided, in accordance with an embodiment of the present invention, apparatus including:

a chamber, which is adapted to be implanted in a body of an individual, the chamber including functional cells and chlorophyll-containing elements;

a light source, configured to provide light to the chlorophyll-containing elements; and a control unit, adapted to drive the light source to provide the light in a series of pulses.

For some applications, the chlorophyll-containing elements include chlorophyll of algae cells. Alternatively or additionally, the chlorophyll-containing elements include chlorophyll of an obligate photoautotroph.

For some applications, the control unit is adapted to configure each of the pulses to have a duration of between 50 and 1000 nanoseconds. Alternatively, the control unit is adapted to configure each of the pulses to have a duration of between 1 and 5000 microseconds.

For some applications, the control unit is adapted to drive the light source to withhold applying light between successive pulses for a period having a duration of between 5000 and 10,000 nanoseconds.

For some applications, the control unit is adapted to configure each of the pulses to have a duration of between 700 and 900 nanoseconds, and to drive the light source to withhold applying light between successive pulses for a period having a duration of between 4000 and 6000 nanoseconds.

For some applications, the light source includes one or more LEDs.

For some applications, the light source is physically coupled to the chamber. Alternatively, the light source is configured to be implanted in the body in a vicinity of the chamber. Further alternatively, the light source is configured to be placed external to the body in a vicinity of the chamber.

For some applications, the chlorophyll-containing elements are positioned in a vicinity of the functional cells in a manner that facilitates consumption by the chlorophyll-containing elements of carbon dioxide produced by the functional cells.

For some applications, the functional cells are mixed with the chlorophyll-containing elements.

For some applications, the chamber includes a matrix, in which the functional cells are dispersed. For some applications, the chamber includes a gel matrix, in which the functional cells and the chlorophyll-containing elements are embedded.

For some applications, the chamber is coated with a vascular growth factor.

For some applications, at least a portion of the chlorophyll-containing elements include intact photosynthetic cells. Alternatively or additionally, at least a portion of the chlorophyll-containing elements include isolated chloroplasts.

For some applications, the light source is configured to provide light having a wavelength of between 400 and 800 nm, such as between 630 and 670 nm.

For some applications, the control unit is adapted to provide the light during less than 90% of a time period having a duration of at least 24 hours, such as less than 50% of the time period, e.g., less than 10% of the time period.

In an embodiment, the control unit is adapted to drive the light source to provide the light intermittently during alternating "on" and "off" periods. For some applications, each of the "on" periods has a duration of between 0.5 minutes and 5 minutes. Alternatively, each of the "on" periods has a duration of between 5 minutes and 5 hours. For some applications, each of the "off" periods has a duration of between 0.5 minutes and 5 minutes. Alternatively, each of the "off" periods has a duration of between 5 minutes and 5 hours.

For some applications, each of the "on" periods has a duration equal to between 10% and 1000% of a duration of each of the "off" periods, such as between 50% and 200% of a duration of each of the "off" periods.

In an embodiment, the chamber includes an oxygen reservoir. For some applications, the control unit is adapted to set at least one parameter of the pulses responsively to at least one oxygen storage property of the oxygen reservoir.

For some applications, the control unit is adapted to set at least one parameter of the pulses responsively to at least one sensed parameter selected from the list consisting of: a sensed parameter of the functional cells, and a sensed parameter of the chlorophyll-containing elements. For some applications, the apparatus includes an oxygen sensor for determining an oxygen concentration in the chamber, the at least one sensed parameter includes the oxygen concentration, and the control unit is adapted to set the at least one parameter of the pulses responsively to the oxygen concentration.

In an embodiment, the chlorophyll-containing elements are positioned in a vicinity of the functional cells in a manner that facilitates providing of oxygen by the chlorophyll-containing elements to the functional cells. For some applications, the control unit is adapted to control a level of the oxygen provided by the chlorophyll-containing elements, by setting at least one parameter of the pulses.

In an embodiment, the functional cells are capable of releasing a substance, and the chamber includes one or more walls that are permeable to the substance and are substantially not permeable to the functional cells, such that the substance is released to the body. For some applications, the functional cells are selected from the list consisting of: pancreatic islet cells, hepatocytes, thyroid cells, parathyroid cells, neural cells, ovarian cells, adrenal cells, renal cortex cells, vascular endothelial cells, thymic cells, ovarian cells, testicular cells, genetically engineered cells, cloned cells, and stem cells. Alternatively, the functional cells include pancreatic beta cells.

In an embodiment, the functional cells are capable of performing at least one of the actions selected from the list consisting of: absorbing a substance from the body, and degrading a substance from the body. For some applications, the functional cells include hepatic cells.

For some applications, the control unit is adapted to determine an indication of a level in the body of a substance to which the functional cells are sensitive. For some applications, the control unit is adapted to determine the indication by monitoring a property selected from the list consisting of: a property of the functional cells and a property of the chlorophyll-containing elements. For some applications, the substance includes glucose, and the control unit is adapted to determine the indication of the level of the glucose. For some applications, the functional cells include pancreatic beta cells.

There is additionally provided, in accordance with an embodiment of the present invention, apparatus for use with functional cells, the apparatus including:

a chamber, which is adapted to be implanted in a body of an individual, and to hold the functional cells, the chamber including chlorophyll-containing elements;

a light source, configured to provide light to the chlorophyll-containing elements; and a control unit, adapted to drive the light source to provide the light in a series of pulses.

There is yet additionally provided, in accordance with an embodiment of the present invention, apparatus including a chamber, which is adapted to be implanted in a body of an individual, the chamber including:

functional cells;

chlorophyll-containing elements; and an oxygen reservoir.

For some applications, at least a portion of the chlorophyll-containing elements include intact photosynthetic cells. Alternatively or additionally, at least a portion of the chlorophyll-containing elements include isolated chloroplasts. For some applications, the chlorophyll-containing elements include chlorophyll of algae cells. For some applications, the chlorophyll-containing elements include chlorophyll of an obligate photoautotroph.

For some applications, at least one of the functional cells and the chlorophyll-containing elements is contained in the oxygen reservoir.

For some applications, the chamber is coated with a vascular growth factor.

For some applications, the oxygen reservoir includes a perfluorocarbon compound. Alternatively or additionally, the oxygen reservoir includes hemoglobin. Further alternatively or additionally, the oxygen reservoir includes silicone.

For some applications, the oxygen reservoir includes a water-based material. For some applications, the water-based material includes a hydrogel, such as alginate and/or agarose.

For some applications, the oxygen reservoir includes a gel matrix. For some applications, the functional cells and the chlorophyll-containing elements are embedded in the gel matrix.

For some applications, the apparatus includes a light source, configured to provide light to the chlorophyll-containing elements; and a control unit, adapted to drive the light source to provide the light in a series of pulses. For some applications, the control unit is adapted to set at least one parameter of the pulses responsively to at least one oxygen storage property of the oxygen reservoir.

There is still additionally provided, in accordance with an embodiment of the present invention, apparatus for use with functional cells, the apparatus including a chamber, which is adapted to be implanted in a body of an individual, and to hold the functional cells, the chamber including:

chlorophyll-containing elements; and an oxygen reservoir.

There is still further provided, in accordance with an embodiment of the present invention, apparatus including:

a chamber, which is adapted to be implanted subcutaneously in a body of an individual, the chamber including functional cells; and an oxygen generator, adapted to be placed outside the body in a vicinity of the skin, and to convey oxygen through the skin to the functional cells.

For some applications, the oxygen generator is adapted to be placed directly against the skin.

For some applications, the apparatus includes a treatment unit, adapted to treat the skin in a manner that enhances oxygen diffusion therethrough.

For some applications, the oxygen generator is adapted to utilize electrolysis to generate oxygen.

For some applications, the chamber is coated with a vascular growth factor.

For some applications, the oxygen generator is adapted to be placed within between 1 mm and 15 mm of the skin. For some applications, the oxygen generator is adapted to be placed within 10 mm of the skin.

For some applications, the apparatus includes a control unit, adapted to activate and inactive the oxygen generator. For some applications, the control unit is configured to activate the oxygen generator when an oxygen concentration in a vicinity of the functional cells is below a first threshold, and to inactivate the oxygen generator when the oxygen concentration in the vicinity of the functional cells is above a second threshold.

In an embodiment, the functional cells are capable of releasing a substance, and the chamber includes one or more walls that are permeable to the substance and are substantially not permeable to the functional cells, such that the substance is released to the body. For some applications, the functional cells are selected from the list consisting of: pancreatic islet cells, hepatocytes, thyroid cells, parathyroid cells, neural cells, ovarian cells, adrenal cells, renal cortex cells, vascular endothelial cells, thymic cells, ovarian cells, testicular cells, genetically engineered cells, cloned cells, and stem cells. Alternatively, the functional cells include pancreatic beta cells.

In an embodiment, the functional cells are capable of performing at least one of the actions selected from the list consisting of: absorbing a substance from the body, and degrading a substance from the body. For some applications, the functional cells include hepatic cells.

For some applications, the apparatus includes a control unit adapted to determine an indication of a level in the body of a substance to which the functional cells are sensitive. For some applications, the control unit is adapted to determine the indication by monitoring a property of the functional cells.

For some applications, the substance includes glucose, and the control unit is adapted to determine the indication of the level of the glucose. For some applications, the functional cells include pancreatic beta cells.

There is also provided, in accordance with an embodiment of the present invention, apparatus for use with functional cells, the apparatus including:

a chamber, which is adapted to be implanted subcutaneously in a body of an individual, and to hold the functional cells; and an oxygen generator, adapted to be placed outside the body in a vicinity of the skin, and to convey oxygen through the skin to the functional cells.

There is further provided, in accordance with an embodiment of the present invention, apparatus including a chamber, which is adapted to be implanted in a body of an individual, the chamber including:

functional cells;
chlorophyll-containing elements; and
a gas-permeable, liquid-impermeable membrane, configured to separate the chlorophyll-containing elements from at least one of: (a) the functional cells, and (b) a fluid of the body.

For some applications, the membrane is configured to separate the chlorophyll-containing elements from the functional cells. Alternatively or additionally, the membrane is configured to separate the chlorophyll-containing elements from the fluid of the body. Alternatively, the membrane is configured to separate the chlorophyll-containing elements from the functional cells and the fluid of the body.

For some applications, the chlorophyll-containing elements include chlorophyll of algae cells.

For some applications, the chamber includes an oxygen reservoir.

In an embodiment, the functional cells are capable of releasing a substance, and the chamber includes one or more walls that are permeable to the substance and are substantially not permeable to the functional cells, such that the substance is released to the body.

In an embodiment, the functional cells are capable of performing at least one of the actions selected from the list consisting of: absorbing a substance from the body, and degrading a substance from the body.

In an embodiment, the apparatus includes a light source, configured to provide light to the chlorophyll-containing elements. For some applications, the apparatus includes a control unit, adapted to drive the light source to provide the light in a series of pulses. Alternatively or additionally, the apparatus includes a control unit, adapted to drive the light source to provide the light intermittently during alternating "on" and "off" periods.

There is still further provided, in accordance with an embodiment of the present invention, a method including implanting, in a body of an individual, a chamber holding functional cells and chlorophyll-containing elements that include chlorophyll of an obligate photoautotroph.

There is also provided, in accordance with an embodiment of the present invention, a method including loading, into a chamber adapted to be implanted in a body of an individual, functional cells and chlorophyll-containing elements that include chlorophyll of an obligate photoautotroph.

There is further provided, in accordance with an embodiment of the present invention, a method including:
implanting, in a body of an individual, a chamber holding functional cells and chlorophyll-containing elements; and
providing light, in a series of pulses, to the chlorophyll-containing elements.

There is still further provided, in accordance with an embodiment of the present invention, a method including implanting, in a body of an individual, a chamber including an oxygen reservoir and holding functional cells and chlorophyll-containing elements.

There is additionally provided, in accordance with an embodiment of the present invention, a method including:
subcutaneously implanting, in a body of an individual, a chamber holding functional cells;
generating oxygen outside the body; and
conveying the oxygen through the skin to the functional cells.

There is yet additionally provided, in accordance with an embodiment of the present invention, a method including:
placing functional cells and chlorophyll-containing elements in a chamber;
separating, using a gas-permeable, liquid-impermeable membrane, the chlorophyll-containing elements from at least one of: (a) the functional cells and (b) fluid of the body; and
implanting the chamber in a body of an individual.

The present invention will be more fully understood from the following detailed description of embodiments thereof, taken together with the drawings, in which:

DETAILED DESCRIPTION OF EMBODIMENTS

Figure 1:
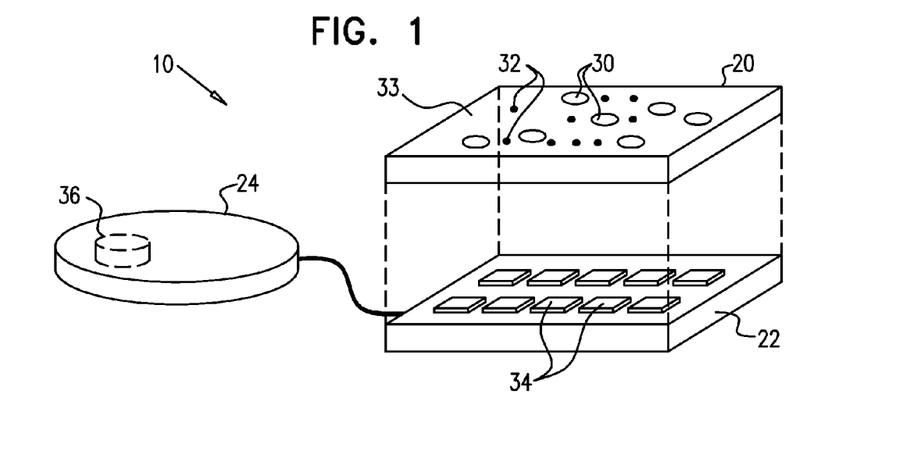
FIG. 1 is a schematic illustration of apparatus for holding functional cells, in accordance with an embodiment of the present invention.

FIG. 1 is a schematic illustration of apparatus 10, in accordance with an embodiment of the present invention. Apparatus 10 comprises a chamber 20, a light source 22, and a control unit 24. Chamber 20 is adapted to be implanted in a body of a subject, and comprises functional cells 30 and chlorophyll-containing elements 32. (Elements in the figures, such as functional cells 30 and chlorophyll-containing elements 32, are shown highly schematically, and are not drawn to scale.) Typically, chlorophyll-containing elements 32 include intact photosynthetic cells and/or isolated chloroplasts. Chlorophyll-containing elements 32 provide oxygen to functional cells 30 and/or consume carbon dioxide produced by functional cells 30. Chamber 20 typically contains a gel matrix 33, in which functional cells 30 and chlorophyll-containing elements 32 are embedded. Gel matrix 33 comprises, for example, alginate, polylysine, chitosan, polyvinyl alcohol, polyethylene glycol, agarose, gelatin, or k-carrageenan. For some applications, in addition to or instead of gel matrix 33, chamber 20 comprises one or more microalgae-compatible fluids. Apparatus 10 typically, but not necessarily, has a total volume of less than 200 cc, e.g., less than 50 cc.

Chamber 20 has one or more walls that are adapted to be permeable to nutrients and substances produced, secreted, uptaken, and/or absorbed by functional cells 30 and/or chlorophyll-containing elements 32. The walls also typically immunoisolate the cells from constituents of the body. For example, the walls may comprise a polyvinyl chloride acrylic copolymer, a cellulose ester, cellulose acetate, or a biocompatible polymer. For some applications, the walls comprise a material adapted to slowly release an anti-fibrosis factor and/or anti-inflammatory factor (e.g., cortisone). Typically, the molecular weight cutoff of the walls is between about 50 and about 500,000 Dalton, such as between about 50 and about 1,000 Dalton, between about 1,000 and about 10,000 Dalton, between about 10,000 and about 40,000 Dalton, between about 40,000 and about 70,000 Dalton, between about 70,000 and about 250,000 Dalton, or between about 250,000 and about 500,000 Dalton. For some applications, the walls are coated with an anti-fibrin coating that can inhibit fibrotic overgrowth.

Typically, chamber 20 is adapted to hold functional cells 30 mixed with chlorophyll-containing elements 32, such that functional cells 30 are not isolated from chlorophyll-containing elements 32. Alternatively, chamber 20 comprises two or more compartments (for example, separated by one or more membranes), some of which compartments hold functional cells 30 and others of which hold chlorophyll-containing elements 32. For example, techniques may be used that are described in the above-mentioned '983 and '069 patent applications to Vardi et al., with reference to FIGS. 1A and 1B thereof. For some applications, chlorophyll-containing elements 32 are separated from functional cells 30 and/or other body fluids by a gas-permeable, liquid-impermeable membrane. For some applications, functional cells 30 and/or chlorophyll-containing elements 32 are dispersed within a liquid medium or matrix in chamber 20. Alternatively or additionally, functional cells 30 and/or chlorophyll-containing elements 32 are coupled to a substrate, such as one or more walls of chamber 20.

For some applications, chamber 20 is adapted to be implanted under skin of the subject, or in the peritoneum. For some applications, the chamber is shaped as a prism (e.g., a rectangular prism, as shown in FIG. 1), an elongated tubular element, a wafer, a sphere, or another shape appropriate for the particular application.

In an embodiment of the present invention, chamber 20 comprises an oxygen reservoir, which typically comprises a material that stores and releases oxygen, such as responsively to an oxygen concentration in a vicinity of the reservoir. Exemplary materials that may serve as the oxygen reservoir include, but are not limited to., a perfluorocarbon compound, hemoglobin, silicone, a water-based material (e.g., a hydrogel such as alginate or agarose or a mixture thereof), and materials described in the above-mentioned U.S. Pat. No. 6,630,154. For some applications, gel matrix 33 comprises and/or serves as the oxygen reservoir. The oxygen reservoir typically stores a portion of the oxygen produced by chlorophyll-containing elements 32 that is in excess of the current needs of functional cells 30, and releases the stored oxygen if insufficient oxygen is later generated by the chlorophyll-containing elements.

Light source 22 is adapted to provide light to chlorophyll-containing elements 32. For some applications, light source 22 comprises LEDs 34, which may, for example, be arranged in an array. Typically, light source 22 is configured to generate light having one or more wavelengths between about 400 and about 800 nm, such as between about 630 and about 670. For some applications, light source 22 is physically coupled to at least one wall of chamber 20, while for other applications, light source 22 is not coupled to the chamber, but is instead adapted to be positioned in a vicinity of the chamber, either implanted in the subject or external to the subject. In this latter case, for some applications the light from light source 22 passes through the subject's skin, in order to reach the rest of apparatus 10.

Control unit 24 is configured to drive light source 22 to provide appropriate light to chamber 20, typically to maintain an oxygen concentration of between about 30 and about 120 mmHg. In an embodiment of the present invention, control unit 24 is configured to intermittently drive light source 22 in alternating "on" and "off" periods, with the light source providing light during the "on" periods, but not during the "off" periods. For example, each of the "on" periods may have a duration of between about 0.5 minutes and about 5 minutes, or between about 5 minutes and about 5 hours, and each of the "off" periods may have a duration of between about 0.5 minutes and about 5 minutes, or between about 5 minutes and about 5 hours. The duration of each "on" period is typically between about 10% and about 1000% of the duration of each "off" period, such as between about 50% and about 200% of the duration of each "off" period.

For applications in which chamber 20 comprises an oxygen reservoir and control unit 24 is configured to intermittently drive light source 22 in alternating "on" and "off" periods, the oxygen reservoir typically stores a portion of the oxygen produced by chlorophyll-containing elements 32 using light absorbed by elements 32 during the "on" periods, and releases the stored oxygen for use by functional cells 30 when chlorophyll-containing elements 32 are not producing oxygen. For some applications, control unit 24 is configured to set at least one parameter of the "on" and/or "off" periods responsively to at least one oxygen storage property of the oxygen reservoir.

Providing the light during alternating "on" and "off" periods generally prevents the oxidation of chlorophyll-containing elements 32 that might otherwise occur at some light intensities useful for illuminating elements 32, given the relatively high density of elements 32.

Figure 2:
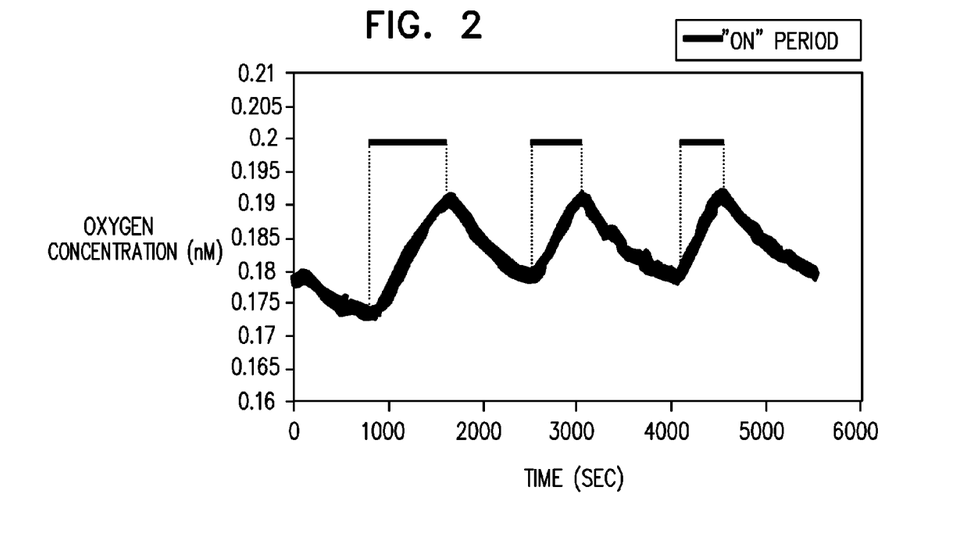
FIG. 2 is a graph showing experimental results measured in accordance with an embodiment of the present invention.

Reference is made to FIG. 2, which is a graph showing experimental results measured in accordance with an embodiment of the present invention. Unicellular algae were immobilized in a slab-shaped alginate gel matrix. The matrix was illuminated in alternating "on" and "off" periods, each "on" period having a duration of about 5 minutes, and each "off" period having a duration of about 5 minutes. The oxygen concentration within the matrix was measured using a needle-type Clark oxygen electrode. As can be seen in the graph, during the "on" periods the oxygen concentration in the matrix increased, as the matrix stored oxygen produced by photosynthesis that occurred in the algae. During the "off" periods, the oxygen concentration in the matrix decreased, as the algae consumed the stored oxygen.

In an embodiment of the present invention, control unit 24 is configured to drive light source 22 to provide the light in a series of pulses, e.g., square pulses. For example, each of the pulses may have a duration of between about 50 and about 1000 nanoseconds, or of between about 1 and about 5000 microseconds, followed by a period during which light is not provided, having a duration of between about 4000 and about 10,000 nanoseconds. For example, light may be provided during periods each having a duration of between about 700 and 900 nanoseconds, e.g., about 800 nanoseconds, separated by periods each having a duration of about 4000 to about 6000 nanoseconds, e.g., about 5000 nanoseconds, during which light is not provided. For some applications, these light-application and non-application periods correspond to the natural periods during which chlorophyll generally absorbs and utilizes light energy, respectively. For applications in which control unit 24 is configured to drive light source 22 in alternating "on" and "off" periods, the control unit drives the light source to apply the series of pulses only during the "on" periods.

Providing the light in a series of pulses generally reduces power consumption of apparatus 10, and/or provides control of the quantity of oxygen produced by chlorophyll-containing elements 32, and/or provides control of the quantity of carbon dioxide consumed by chlorophyll-containing elements 32. In addition, providing the light in a series of pulses generally prevents the oxidation of chlorophyll-containing elements 32 that might otherwise occur at light intensities necessary to sufficiently illuminate elements 32 given the relatively high density of elements 32.

For some applications, control unit 24 adjusts one or more parameters of the pulses and/or the "on"/"off" periods responsively to one or more sensed parameters of functional cells 30 and/or chlorophyll-containing elements 32. For example, chamber 20 may comprise an oxygen sensor (not shown) that detects an oxygen concentration in a vicinity of functional cells 30, and/or in a vicinity of chlorophyll-containing elements 32.

Apparatus 10 typically comprises a power source 36, which is located in control unit 24, in chamber 20, or elsewhere implanted in or external to the body of the subject. Typically, power source 36 comprises a battery, which may be rechargeable, either wirelessly or over wires.

In an embodiment of the present invention, chlorophyll-containing elements 32 include chlorophyll of an obligate photoautotroph. As used in the present application, including the claims, an obligate photoautotroph is an organism that, under conditions of ordinary use of apparatus 10, produces energy substantially only by photosynthesis, and substantially cannot use organic materials in the surrounding environment as a source of energy. As a result, such obligate photoautotrophs are substantially unable to grow in organic media in the dark. (See, for example, Smith A J, "Acetate assimilation by *Nitrobacter agilis* in relation to its 'obligate autotrophy,'" Journal of Bacteriology 95:844-855 (1968), which is incorporated herein by reference.) Appropriate obligate photoautotrophs include, but are not limited to, certain of the cyanobacteria (formerly called blue-green algae), certain of the *thiobacilli*, and bacteria of the genus *Chlorobium*.

Alternatively or additionally, chlorophyll-containing elements 32 include unicellular algae, or other autotrophic or mixotrophic photosynthetic cells.

In an embodiment of the present invention, functional cells 30 include beta cells, alpha cells, other pancreatic islet cells, hepatic cells, neural cells, renal cortex cells, vascular endothelial cells, thyroid cells, parathyroid cells, adrenal cells, thymic cells, ovarian cells, and/or testicular cells.

In an embodiment of the present invention, apparatus 10 is configured to:
  treat a condition characterized by an insufficiency or lack of a natural population of the functional cells, or by reduced effectiveness of such cells, which results in an insufficient supply of a beneficial substance secreted by the cells, such as a hormone or a neurotransmitter. Functional cells 30 held in chamber 20 secrete the beneficial substance. For example, functional cells 30 may include beta cells, and apparatus 10 may be configured to treat type I or type II diabetes. "Beta cells," as used herein, including in the claims, includes isolated beta cells and/or beta cells within islets and/or stem-cell-derived insulin-producing cells, and/or tumor-derived insulin-producing cells, and/or engineered insulin-producing cells, and/or transdifferentiated non-beta-cell-derived insulin-producing cells, and/or any insulin-producing cells, and/or a mixture of various sources of insulin-producing cells.
  treat a condition characterized by an insufficiency or lack of a natural population of the functional cells, or by reduced effectiveness of such cells, which results in insufficient uptake, absorption, and/or degradation of a substance (e.g., a toxic substance) by the cells. For example, functional cells 30 may include hepatic cells, and apparatus 10 may be configured to uptake various toxic substances.
  sense a level of a bodily constituent to which functional cells 30 are sensitive. Apparatus 10 is configured to sense the constituent by monitoring a property of functional cells 30 and/or of chlorophyll-containing elements 32 that generally correlates with a level of the constituent. For example, apparatus 10 may monitor a level of oxygen produced by chlorophyll-containing elements 32. Alternatively or additionally, apparatus 10 is adapted to use techniques for monitoring an electrical or optical property of functional cells 30 to detect a constituent such as glucose, as described in the above-mentioned U.S. Pat. No. 5,101,814. For some applications, functional cells 30 include beta cells, and apparatus 10 is configured to sense a glucose level by directly or indirectly monitoring activity of the beta cells.

For applications in which functional cells 30 include beta cells, the number of islets containing beta cells typically is between about 10,000 and about 600,000 (e.g., between about 100,000 and about 600,000), and/or the number of beta cells is typically between about 10 million and about 600 million (e.g., between about 100 million and about 600 million). These numbers of islets and/or beta cells are believed by the inventors to be lower than those typically used in conventional beta cell implantation techniques, at least in part because of the higher oxygen concentrations available to the beta cells using the techniques described herein. For some applications, functional cells 30 include fewer than 10,000 islets and/or fewer than 10 million beta cells. For some applications, the beta cells proliferate after implantation, thereby increasing their number after implantation.

For some applications, the functional cells include individual cells, cell clusters, or pieces of excised tissue. The tissue or cells may include, for example, tissue or cells removed from a donor animal, tissue or cells obtained by incubation or cultivation of donor tissue and cells, cells obtained from viable cell lines, and/or cells obtained by genetic engineering. For some applications, the tissue or cells are of human or animal origin. Alternatively or additionally, the tissue or cells are genetically engineered, cloned cells, and/or derived from stem cells. For some applications, the tissue or cells are autologous; alternatively, the tissue or cells are heterologous with respect to the subject's cells.

Figure 3A:
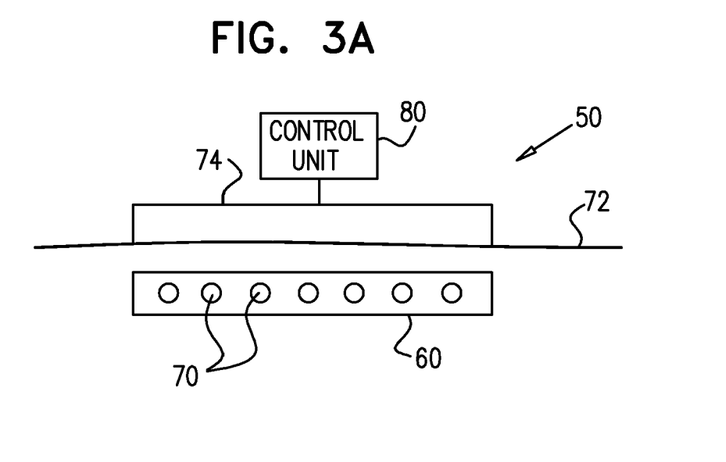
FIGS. 3A-B are schematic cross-sectional illustrations of another apparatus for holding functional cells, in accordance with an embodiment of the present invention.
Figure 3B:
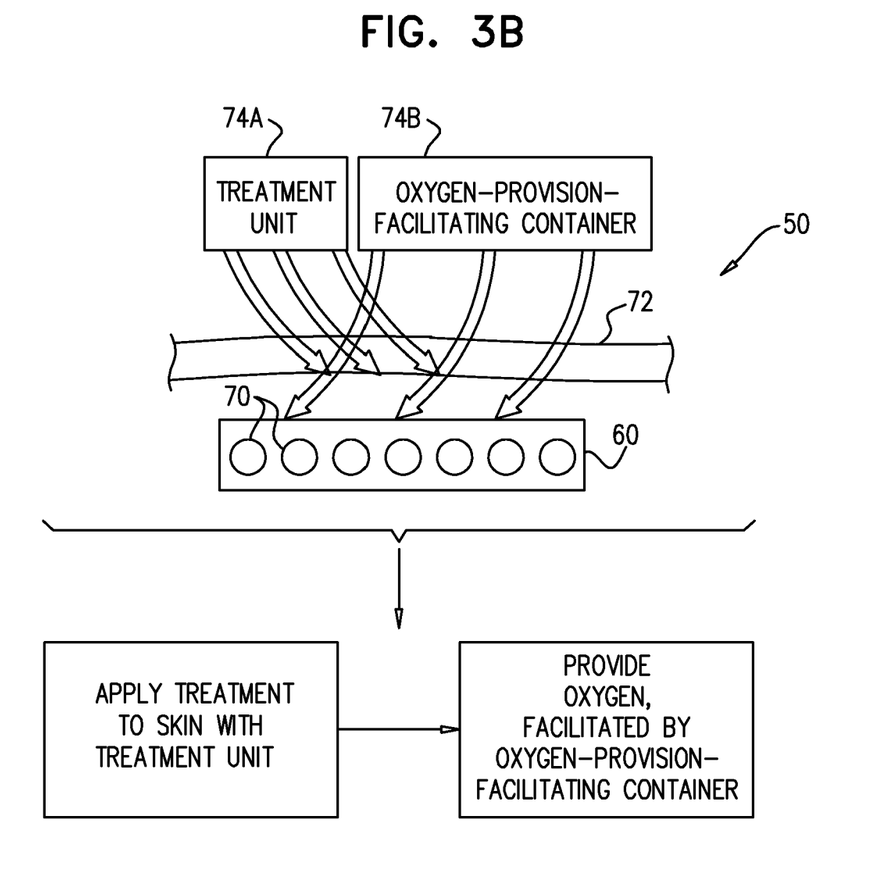

Reference is now made to FIGS. 3A-B, which are schematic cross-sectional illustrations of apparatus 50, in accordance with an embodiment of the present invention. Apparatus 50 comprises a chamber 60, which comprises functional cells 70. Except as described hereinbelow, chamber 60 is generally similar to chamber 20, described hereinabove with reference to FIG. 1. Chamber 60 typically does not comprise chlorophyll-containing elements. Chamber 60 is adapted to be implanted subcutaneously under skin 72 in a body of a subject. As shown in FIG. 3A, apparatus 50 further comprises an oxygen generator 74, adapted to be placed outside the body in a vicinity of skin 72. Typically, oxygen generator 74 is adapted to be placed directly against the skin. Oxygen generator 74 generates oxygen, which passes through skin 72 and into chamber 60, where functional cells 70 can utilize the oxygen. For some applications, skin 72 is pre-treated in order to enhance oxygen diffusion therethrough. The pre-treatment may include mechanical, electrical, chemical, and/or biochemical (e.g., VEGF) pre-treatment. For example, electrical pre-treatment may be applied using techniques described in U.S. Pat. No. 6,148,232 to Avrahami. Oxygen generator 74 may, for example, utilize electrolysis, or other techniques known for generating oxygen. For some applications, oxygen generator 74 comprises a small container, such as a cylinder, e.g., with a length of about 8 cm and a diameter of about 1 cm.

FIG. 3B shows a treatment unit 74A and an oxygen-provision-facilitating container 74B. Treatment unit 74A is configured to treat skin 72 in a manner that facilitates oxygen transport from oxygen-provision-facilitating container 74B therethrough.

In an embodiment of the present invention, prior to implanting chamber 20 (FIG. 1) or chamber 60 (FIG. 3), a vascular growth factor is applied in a vicinity of the implantation site. For example, the vascular growth factor may be applied several days or several weeks prior to implantation. The vascular growth factor generally increases capillary growth in the vicinity of the implantation site, which generally enhances oxygen delivery to the chamber via the blood circulation. Vascular growth factors include, for example, vascular endothelial growth factor (VEGF), platelet derived growth factor (PDGF), vascular permeability growth factor (VPF), basic fibroblast growth factor (bFGF), or transforming growth factor beta (TGF-β).

In an embodiment of the present invention, chamber 20 or chamber 60 is coated with a vascular growth factor prior to implantation. For example, techniques may be used that are described in U.S. Pat. No. 5,443,508 to Giampapa, which is incorporated herein by reference.

For some applications, apparatus 50 comprises a control unit 80, which is adapted to activate and inactivate oxygen generator 74. For some applications, control unit 80 is configured to activate oxygen generator 74 when an oxygen concentration in a vicinity of functional cells 70 is below a first threshold (e.g., a threshold between about 30 and about 50 mmHg, such as about 40 mmHg), and to inactivate oxygen generator 74 when the oxygen concentration in the vicinity of functional cells 70 is above a second threshold (e.g., a threshold between about 80 and about 100 mmHg).

For some applications, techniques described herein are performed in combination with techniques described in the above-mentioned '983 and '069 patent applications to Vardi et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a chamber, which is adapted to be implanted subcutaneously in a body of an individual, the chamber comprising therein functional cells isolated by the chamber;
   an oxygen-provision-facilitating container, adapted to be placed outside the body in a vicinity of skin of the individual, and to convey oxygen through the skin to the functional cells; and
   a treatment unit adapted to treat the skin of the individual in a manner that facilitates oxygen transport therethrough.

2. The apparatus according to claim 1, wherein the oxygen-provision-facilitating container is adapted to be placed directly against the skin.

3. The apparatus according to claim 1, wherein the oxygen-provision-facilitating container is adapted to utilize electrolysis to generate oxygen.

4. The apparatus according to claim 1, wherein the chamber is coated with a vascular growth factor.

5. The apparatus according to claim 4, wherein the chamber is coated with one or more factors selected from the group consisting of: vascular endothelial growth factor (VEGF), platelet derived growth factor (PDGF), vascular permeability growth factor (VPF), basic fibroblast growth factor (bFGF), and transforming growth factor beta (TGF-.beta.).

6. The apparatus according to claim 1, wherein the oxygen-provision-facilitating container is adapted to be placed within between 1 mm and 15 mm of the skin.

7. The apparatus according to claim 1, wherein the functional cells are capable of releasing a substance, and wherein the chamber comprises one or more walls that are permeable to the substance and are substantially not permeable to the functional cells, such that the substance is released to the body.

8. The apparatus according to claim 7, wherein the functional cells are selected from the list consisting of: thyroid cells, parathyroid cells, neural cells, ovarian cells, adrenal cells, renal cortex cells, vascular endothelial cells, thymic cells, ovarian cells, testicular cells, genetically engineered cells, cloned cells, and stem cells.

9. The apparatus according to claim 7, wherein the functional cells comprise pancreatic beta cells.

10. The apparatus according to claim 9, wherein the chamber comprises between 10 million and 600 million of the beta cells.

11. The apparatus according to claim 9, wherein the chamber comprises fewer than 10 million of the beta cells.

12. The apparatus according to claim 1, wherein the functional cells are capable of performing at least one action selected from the group consisting of: absorbing a substance from the body, and degrading a substance from the body.

13. The apparatus according to claim 12, wherein the functional cells comprise hepatic cells.

14. The apparatus according to claim 1, wherein the chamber is shaped so as to define a wafer.

15. The apparatus according to claim 1, wherein the treatment unit comprises an electrical treatment unit.

16. The apparatus according to claim 1, wherein the treatment unit comprises a mechanical treatment unit.

17. The apparatus according to claim 1, wherein the chamber comprises one or more walls, adapted to immunoisolate the functional cells from constituents of the body.

18. The apparatus according to claim 1, wherein the chamber comprises a gel matrix, in which the functional cells are embedded.

19. The apparatus according to claim 1, wherein the chamber comprises an oxygen reservoir.

20. The apparatus according to claim 19, wherein the oxygen reservoir comprises a material that stores and releases oxygen responsively to an oxygen concentration in a vicinity of the reservoir.

21. The apparatus according to claim 20, wherein the oxygen reservoir comprises a perfluorocarbon compound.

22. The apparatus according to claim 20, wherein the oxygen reservoir comprises hemoglobin.

23. The apparatus according to claim 20, wherein the oxygen reservoir comprises silicone.

24. The apparatus according to claim 20, wherein the oxygen reservoir comprises a water-based material.

25. The apparatus according to claim 24, wherein the water-based material comprises a hydrogel.

26. The apparatus according to claim 25, wherein the hydrogel is selected from the list consisting of: alginate and agarose.

27. The apparatus according to claim 20, wherein the oxygen reservoir comprises a gel matrix.

28. The apparatus according to claim 27, wherein the functional cells are embedded in the gel matrix.

29. The apparatus according to claim 1, wherein the chamber comprises between 10,000 and 600,000 pancreatic islets.

30. Apparatus for use with functional cells, the apparatus comprising:
   a chamber, which is adapted to be implanted subcutaneously in a body of an individual, and to hold the functional cells isolated by the chamber;

an oxygen-provision-facilitating container, adapted to be placed outside the body in a vicinity of skin of the individual, and to convey oxygen through the skin to the functional cells; and a treatment unit adapted to treat the skin of the individual in a manner that facilitates oxygen transport therethrough.

* * * * *